United States Patent
Leinweber et al.

(10) Patent No.: US 10,993,898 B2
(45) Date of Patent: May 4, 2021

(54) FATTY ACID ESTERS OF OXALKYLATED ALKYLALKYLENEDIAMINES AND SALTS THEREOF AND COMPOSITIONS FOR CONDITIONING OF HAIR

(71) Applicant: Clariant International Ltd., Muttenz (CH)

(72) Inventors: Dirk Leinweber, Kelkheim (DE);
Hannah Benson, Bensheim (DE);
Henrike Neuhoff, Hannover (DE);
Katarzyna Kita-Tokarczyk, Bad Soden (DE)

(73) Assignee: Clariant International Ltd., Muttenz (CH)

( * ) Notice: Subject to any disclaimer, the term of this patent is extended or adjusted under 35 U.S.C. 154(b) by 308 days.

(21) Appl. No.: 15/038,668

(22) PCT Filed: Jan. 23, 2015

(86) PCT No.: PCT/EP2015/000136
§ 371 (c)(1),
(2) Date: May 23, 2016

(87) PCT Pub. No.: WO2015/110269
PCT Pub. Date: Jul. 30, 2015

(65) Prior Publication Data
US 2016/0317410 A1    Nov. 3, 2016

(30) Foreign Application Priority Data

Jan. 23, 2014 (EP) .................................... 14152291

(51) Int. Cl.
| | | |
|---|---|---|
| *A61Q 5/12* | (2006.01) | |
| *A61K 8/45* | (2006.01) | |
| *A61K 8/34* | (2006.01) | |
| *A61K 8/41* | (2006.01) | |

(52) U.S. Cl.
CPC .............. *A61K 8/45* (2013.01); *A61K 8/342* (2013.01); *A61K 8/416* (2013.01); *A61Q 5/12* (2013.01)

(58) Field of Classification Search
None
See application file for complete search history.

(56) References Cited

U.S. PATENT DOCUMENTS

| | | | |
|---|---|---|---|
| 4,415,487 A | | 11/1983 | Blaschke |
| 4,720,382 A | * | 1/1988 | Erdman .................. A61K 8/416 424/70.1 |
| 4,997,912 A | * | 3/1991 | Wirtz ..................... C07C 217/08 530/232 |
| 5,718,891 A | | 2/1998 | Prat |
| 6,641,803 B1 | | 11/2003 | Kahre |
| 2002/0143063 A1 | * | 10/2002 | Alvarado ........... A61K 49/0043 514/642 |
| 2004/0169161 A1 | | 9/2004 | Dahlmann |
| 2006/0210509 A1 | * | 9/2006 | Johnson .................. A61K 8/416 424/70.12 |

FOREIGN PATENT DOCUMENTS

| | | |
|---|---|---|
| DE | 19810122 | 9/1999 |
| EP | 0081691 | 6/1983 |
| JP | S433001 | 2/1968 |
| JP | H06340598 | 12/1994 |
| JP | H08507538 | 8/1996 |
| JP | 2002505253 | 2/2002 |
| JP | 2002363040 | 12/2002 |

(Continued)

OTHER PUBLICATIONS

English Abstract for JPS433001, dated Feb 3, 1968, (1 page).

(Continued)

*Primary Examiner* — Jyothsna A Venkat
(74) *Attorney, Agent, or Firm* — Tod A. Waldrop

(57) ABSTRACT

Hair conditioner compositions comprising an ester of an oxalkylated alkylalkylene diamine of formula (I)

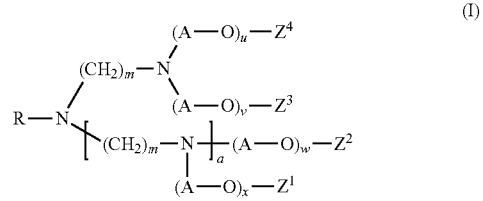

wherein:

R denotes $C_8$-$C_{24}$-alkyl or $C_8$-$C_{24}$-alkenyl

A denotes a group —$C_2H_4$— or —$C_3H_6$ $Z^1$ denotes a group —C(O)—R', wherein R' denotes $C_5$-$C_{35}$-alkyl or $C_5$-$C_{35}$-alkenyl, $Z^2$ denotes a group —C(O)—R", wherein R" denotes $C_5$-$C_{35}$-alkyl or $C_5$-$C_{35}$-alkenyl, $Z^3$ denotes a group —C(O)—R'", wherein R'" denotes $C_5$-$C_{35}$-alkyl or $C_5$-$C_{35}$-alkenyl, $Z^4$ denotes a group —C(O)—R"", wherein R"" denotes $C_5$-$C_{35}$-alkyl or $C_5$-$C_{35}$-alkenyl, a denotes 0 or 1, m denotes 2 or 3, and u, v, w and x are each independently numbers from 1 to 9, or the quaternized salts thereof, and comprising at least one alcohol component, having 6 to 18 carbon atoms, lead to improved conditioning and gloss of the hair.

16 Claims, No Drawings

(56) References Cited

FOREIGN PATENT DOCUMENTS

| JP | 2006052224 | 2/2006 |
|---|---|---|
| WO | 9525713 | 9/1995 |
| WO | 03008668 | 1/2003 |
| WO | 2010051895 | 5/2010 |

OTHER PUBLICATIONS

International Search Report for PCT/EP2015/000136, dated Apr. 29, 2015. (4 pages).
Written Opinion of the International Searching Authority for PCT/EP2015/000136, dated Apr. 29, 2015. (8 pages).
Machine Translation of DE19810122, Goldwell GmbH, 1999, 7 pages.

* cited by examiner

FATTY ACID ESTERS OF OXALKYLATED ALKYLALKYLENEDIAMINES AND SALTS THEREOF AND COMPOSITIONS FOR CONDITIONING OF HAIR

Many methods for the cleaning and conditioning of hair are known for centuries. Often, the methods require an alkaline agent, such as soap. The interaction of this agent with hair results in weakening its mechanical properties and increases the porosity of hair fibers. Many known shampooing components result in dry hair that is damaged. Furthermore, the color of hair often fades with time due to washing and upon exposure to environmental factors such as sun and pollution. This can lead to dull appearance of the hair and results in more frequent washing than required. Frequent washing of hair may result in more damaged and less conditioned hair.

In order to improve the condition of hair and to keep a natural look of the hair over a longer period of time, improved hair care regimens and conditioning compositions are required.

Natural oils have been used for centuries to condition human hair. Essential oils (e.g. tea tree oil) and carrier oils (e.g. jojoba oil) have been used. Human hair contains about 97% of the protein keratin, which needs to be protected to preserve the strength and natural look. The surface of the protein keratin contains negatively charged amino acids. For this reason, hair conditioners can contain cationic components (e.g. surfactants) which are not washed out completely. The hydrophilic ends of the cationic components can bind to the keratin, whereas the hydrophobic ends of the molecules protect the hair surface.

Modern hair conditioner compositions often are intended to soften the hair, to improve the gloss of hair and to avoid a greasy feeling of the hair. Fatty alcohols, silicone derivatives and quaternary ammonium compounds were used for hair conditioner compositions, which coat the cuticle of the hair itself.

Hair conditioner compositions can be used together with a shampoo composition or separately. Hair conditioner compositions comprise one or more of the following types of ingredients (components):
  acidity regulators, which maintain the conditioner's pH at about 3 to 5.
  antistatic agents
  glossers, light-reflecting polymer components binding to the hair surface, such as silicones, e.g., dimethicone or cyclomethicone.
  lubricants, such as fatty alcohols or pro-vitamins, such as panthenol. moisturizers, which hold moisture in the hair and often contain humectants.
  oils (e.g. natural oils) for the hair to become soft and pliable. preservatives, to avoid micro-organisms-growth in the composition.
  sequestrants, for improving the function of the composition in hard water.
  strengtheners, often containing hydrolyzed protein, to penetrate the hair and reinforce the structure, e.g. through polymer crosslinking.
  sun protectors against protein degradation and color loss, e.g.benzophenone.
  surfactants, such as cationic components, for the protection of the hair surface, such as cetyl trimethylammonium chloride (CTAC),
  thermal protectors, e.g. heat-absorbing components.

There still is a need for improved cosmetic compositions, in particular for hair treatment, and for new hair conditioner compositions which, based on easily available components, protect against UV-light, pollution and other negative influences of the environment. Particularly in big cities, with a lot of air pollution, the hair needs to be protected over a long period of time.

Several fatty acid esters of oxalkylated alkylalkylenediamines have been described more than 25 years ago. EP-A 320 769 discloses a process for preparation of oxalkylated alkylalkylenediamines. This document uses the ester compounds (or the mixtures thereof) as corrosion inhibitors, particularly in crude oil recovery plants and crude oil treatment plants. EP-A 320 769 briefly mentions the reaction of oxalkylated alkylalkylenediamines with benzyl chloride or methyl chloride, leading to the respective salts. However, the use of a composition comprising such a compound as hair care products is not mentioned in EP-A 320 769.

The old document EP-A 081 691 (Hoechst) relates to bis-betaines having the following formula, which are used as cleanser.

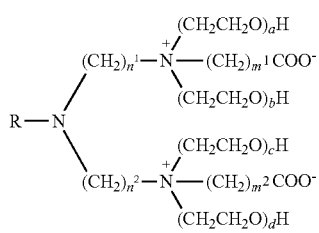

An objective of EP-A 081 691 is to provide "non-irritating to skin and eye mucosa betaines, a process for their preparation, and hair shampoos and cosmetic cleansers comprising these betaines. However, esterified derivatives are not mentioned.

DE-A 19810122 (Goldwell GmbH) discloses hair treatment agents, e.g. $C_{8-18}$-alkyl polyglucosides having the formula $R-O-(R^1O)_n-Z_x$ which are suitable as surfactants. Furthermore, the use of amphoteric surfactants such as alkylamide-betaines are mentioned which are structurally different to compounds of formula (I) of the present application.

WO 95/25713 (Henkel AG) relates to ester-quats which are suitable as surfactant but which are structurally different to compounds of formula (I) of the present application.

WO 2010/0518995 (Clariant) describes a composition of at least one quarternary ammonia compound and at least one amine alkoxylate ester of the following formula:

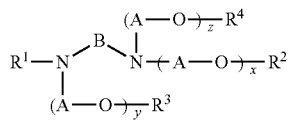

Neither the use of the compounds as hair care agent is mentioned in WO 2010/0518995 nor the use as cleansing agent.

WO 2003/008668 (Clariant) relates to additives which inhibit the corrosion on conveyors and transport devise for hydrocarbons ion crude oil transport and processing, having the formula:

$$\left[\begin{array}{c} R^1 \\ | \\ R^3-N-R^2 \\ | \\ R^4 \end{array}\right]^+ \quad X^-$$

The use of these compounds as hair care agent is not mentioned in WO 03/008668.

It now was found that specific esters of oxalkylated alkylalkylenediamines and/or the quaternized salts thereof, such as the salts formed with dimethyl sulfate, are excellent components in cosmetic compositions, in particular for hair treatment.

The present invention relates to a cosmetic composition, in particular a hair conditioner composition, which comprises as one component at least one ester of an oxalkylated alkylalkylene diamine of formula (I), and/or a quaternized salt thereof, $$R-N\begin{array}{c}(CH_2)_m-N\begin{array}{c}(A-O)_u-Z^4\\(A-O)_v-Z^3\end{array}\\ \left[(CH_2)_m-N\begin{array}{c}(A-O)_w-Z^2\\(A-O)_x-Z^1\end{array}\right]_a\end{array} \quad (I)$$

wherein
R denotes $C_8$-$C_{24}$-alkyl or $C_8$-$C_{24}$-alkenyl, in particular $C_{10}$-$C_{20}$-alkyl or $C_{10}$-$C_{20}$-alkenyl,
A denotes a group —$C_2H_4$— or —$C_3H_6$—, in particular a group —$C_2H_4$—
$Z^1$ denotes a group —C(O)—R', wherein R' denotes $C_5$-$C_{35}$-alkyl or $C_5$-$C_{35}$-alkenyl, in particular $C_8$-$C_{24}$-alkyl or $C_8$-$C_{24}$-alkenyl,
$Z^2$ denotes a group —C(O)—R", wherein R" denotes $C_5$-$C_{35}$-alkyl or $C_5$-$C_{35}$-alkenyl, in particular $C_8$-$C_{24}$-alkyl or $C_8$-$C_{24}$-alkenyl,
$Z^3$ denotes a group —C(O)—R''', wherein R''' denotes $C_5$-$C_{35}$-alkyl or $C_5$-$C_{35}$-alkenyl, in particular $C_8$-$C_{24}$-alkyl or $C_8$-$C_{24}$-alkenyl,
$Z^4$ denotes a group —C(O)—R'''', wherein R'''' denotes $C_5$-$C_{35}$-alkyl or $C_5$-$C_{35}$-alkenyl, in particular $C_8$-$C_{24}$-alkyl or $C_8$-$C_{24}$-alkenyl,
a denotes 0 or 1, in particular 0
m denotes 2 or 3, in particular 3
u, v, w and x are each independently numbers from 1 to 9, in particular 2 to 9
where the sum of u, v, w and x being from 3 to 30, if a=0, and
where the sum of u, v, w and x being from 4 to 35, if a=1.

In one embodiment, the cosmetic composition, in particular hair conditioner composition, comprises as one further component at least one fatty alcohol component, having 6 to 18 carbon atoms. This component can serve as lubricant. Often a mixture of at least two different fatty alcohol components, having 6 to 18 carbon atoms, is used. Cetearyl alcohol (mixture of cetyl- and stearyl-alcohol) is one useful example.

Some of the compounds of formula (I) are known as chemical substances, but others have not been described.

In particular, the quaternized salts of several esters of the oxalkylated alkylalkylene diamines of formula (I) have not been described and are part of this invention.

For the preparation of the quaternized salts, components such as dimethyl sulfate can be used, or more generally compounds of formula $(R^2)_s$-M, where $R^2$ is an $C_1$ to $C_5$-alkyl or benzyl group, M stands for an anion-forming group, such as sulfate, and s denotes 1, 2 or 3. The quaternized salts are often made by formation of groups of the formula $N^+$—$R^2$ $M^-$ where $N^+$ is a quaternized nitrogen, $R^2$ denotes e.g. $C_1$-$C_5$-alkyl and $M^-$ is an anion, such as sulfate.

The invention also relates to a composition, comprising as one component at least one ester of an oxalkylated alkylalkylene diamine of formula (I), wherein
R denotes $C_8$-$C_{24}$-alkyl or $C_5$-$C_{24}$-alkenyl, in particular $C_{10}$-$C_{20}$-alkyl or $C_{10}$-$C_{20}$-alkenyl,
A denotes a group —$C_2H_4$—
$Z^1$ denotes —C(O)—R', wherein R' denotes $C_8$-$C_{18}$-alkyl or $C_8$-$C_{18}$-alkenyl
$Z^2$ denotes —C(O)—R", wherein R" denotes $C_8$-$C_{18}$-alkyl or $C_8$-$C_{18}$-alkenyl
$Z^3$ denotes —C(O)—R''', wherein R''' denotes $C_8$-$C_{18}$-alkyl or $C_8$-$C_{18}$-alkenyl
$Z^4$ denotes —C(O)—R'''', wherein R'''' denotes $C_8$-$C_{18}$-alkyl or $C_8$-$C_{18}$-alkenyl
a denotes 0
m denotes 2 or 3, in particular 3
u, v and w are each independently numbers from 3 to 9
where the sum of u, v and w being from 6 to 30,
and/or a quaternized salt thereof, where the salt is formed by quaternizing one, two or three, in particular one or two, of the nitrogen atoms of compound of formula (I).

The invention also relates to a composition, comprising as one component at least one ester of an oxalkylated alkylalkylene diamine of formula (I), wherein:
R denotes $C_8$-$C_{18}$-alkyl or $C_8$-$C_{18}$-alkenyl
A denotes a group —$C_2H_4$—
$Z^1$,$Z^2$,$Z^3$ and $Z^4$ are the same and denote —C(O)—R'
with
R' being $C_8$-$C_{18}$-alkyl or $C_8$-$C_{18}$-alkenyl
a denotes 0, m denotes 3
u, v and w are each independently numbers from 3 to 9
where the sum of u, v and w being from 6 to 30,
and/or a quaternized salt thereof, where the salt is formed by quaternizing one or two of the nitrogen atoms of the compound of formula (I).

The numbers u, v and w are often the same numbers, ranging from 5 to 9, often from 5.5 to 7.8. Compounds of formula (I) with n from 7 to 7.8 and $(CH_3SO_4)^-$ as anion are of particular interest.

The quaternized salt of the compounds of formula (I) can be formed by quaternizing one or two or more of the nitrogen atoms of the compound of formula (I), e.g. by using an alkylating agent, such as compounds of formula $(R^2)_s$-M, such as dimethyl sulfate, diethyl sulfate, dimethyl carbonate, diethyl carbonate or an alkylhalogenide ($R^2$-Hal), like methyl chloride, ethyl chloride, methyl bromide, ethyl bromide, methyl iodide or ethyliodide. The group $R^2$ denotes preferably $C_1$-$C_5$-alkyl, in p articular methyl or ethyl.

The invention also relates to a composition, comprising as one component at least one quaternized salt of an ester of an oxalkylated alkylalkylene diamine of formula (I).

This cosmetic composition, in particular hair conditioner, often comprises as further component at least one fatty alcohol component, having 6 to 18 carbon atoms.

The invention also relates to a composition, comprising 0.1 to 10% by weight of an ester of an oxalkylated alkyl-alkylene diamine of formula (I), or a quaternized salt thereof (which is a surfactant), and as further components water and 0.5 to 10% by weight of at least one fatty alcohol component (lubricant), having 6 to 18 carbon atoms.

The invention also relates to a composition, comprising as further components at least one acidity regulator, at least one glosser, and at least one further surfactant.

One further aspect of the invention is a method of preparing a cosmetic composition, in particular hair conditioner composition, comprising the step of mixing at least one ester of an oxalkylated alkylalkylene diamine of formula (I), or a quaternized salt thereof, as described above, and at least one further component. The at least one further component preferably is at least one fatty alcohol component, having 6 to 18 carbon atoms.

The invention also relates to a method of conditioning hair, comprising the steps of applying a conditioner composition (comprising as one component at least one ester of formula (I) or a quaternized salt thereof) onto wet hair and then removing said conditioner composition from the hair. The conditioner composition can be used on pre-cleaned hair but also without pre-treatment.

The invention in particular relates to a method of treating the hair, comprising the following steps:
a) applying a shampoo composition onto the hair;
b) washing the hair with the shampoo composition;
c) removing the shampoo composition from the hair;
d) applying a conditioner composition onto wet hair;
e) rinsing said conditioner composition from the hair,
wherein the conditioner composition comprises as one component at least one ester of an oxalkylated alkylalkylene diamine of formula (I), as described above, or a quaternized salt thereof.

The described method of treating hair of the present invention may also include one or more additional steps with additional ingredients, such as a color altering composition, a developer composition, a pre-treatment composition and/or a post-treatment composition. Such ingredients of the additional steps include well-known conventional additives, typically employed in hair treatment compositions, such as coloring agents, basifying and acidifying agents, buffers, thickening agents, gelling agents, rheological modifiers, antioxidants, fragrances and chelating agents.

The invention also relates to a method of treating the hair, wherein said conditioner composition comprises a quaternized salt of an oxalkylated alkylalkylene diamine of formula (I), where the salt is quaternized at one or two of the nitrogen atoms of the compound of formula (I). In one embodiment, the hair conditioner composition comprises at least one fatty alcohol component, having 6 to 18 carbon atoms.

The invention also relates to a method of treating the hair, wherein said conditioner composition further comprises as lubricant at least one fatty alcohol component, having 6 to 18 carbon atoms. Often a mixture of at least two different fatty alcohol components, having 6 to 18 carbon atoms, is used, such as cetearyl alcohol (mixture of cetyl- and stearyl-alcohol).

The invention also relates to a method of treating the hair, wherein the conditioner composition further comprises at least one acidity regulator, at least one glosser, and at least one further surfactant.

The invention also relates to a method of treating the hair, wherein the conditioner composition further comprises at least one further surfactant which is chosen from non-polymeric, cationic quaternary ammonium compounds, in particular CTAC.

The invention also relates to a method of treating the hair, wherein said conditioner composition is applied to the hair on a weekly to bi-weekly basis following initial treatment of the hair with a shampoo composition.

The invention also relates to a multiple-part kit of hair cleaning and hair conditioning compositions. The term "kit" includes items that are either sold or packaged together. The multiple-part kit may be distributed to end users through salons, but one aspect of the invention involves distributing the kits to consumers through retail sales channels such as drugstores, cosmetic stores and on-line stores. The kit comprises separate compartments with formulations for a shampoo and a conditioning treatment. The term "compartment" refers to any receptacle, regardless of shape, material or closure, which serves a containing function.

The term "compartment" includes the interior of a tube, sack, can, tub, bottle, packet, envelope or other vessel. The components of the multiple-part kit may be contained in a single receptacle, or may be divided amongst multiple receptacles. The multiple-part kit can additionally comprise a compartment with a composition to color the hair and/or a composition to moisturize and maintain the quality of the treated hair.

For bleached or colored hair, additional compartments in the multiple-part kit are advantageous. There is a high need for a hair cleaning and hair conditioning kit, that is easy to use and that provides a consumer specialized care regimen to preserve the condition of the hair. The invention provides all this in one multiple-part kit with all the components needed to maintain the condition of the hair for several weeks. The kit may include at least one compartment containing a pre-treatment composition.

This pre-treatment composition may comprise known natural oils, humectants, non-ionic surfactants, cationic conditioning agents (such as the salts of compounds of formula (I)), plant extracts, vitamins, and organic oils.

Suitable organic oils include esters of the formula R'CO—OR", wherein R' and R" are each independently a $C_4$-$C_{20}$ straight or branched chain alkyl, alkenyl or alkoxy-carbonylalkyl or alkylcarbonyl-oxyalkyl. Examples of such esters include isotridecyl isononanoate, PEG-4 diheptanoate, isostearyl neopentanoate, tridecyl neopenta-noate, cetyl octanoate, cetyl palmitate, cetyl ricinoleate, cetyl stearate, cetyl myristate, isopropyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, and fatty alcohols such as oleyl alcohol, isocetyl alcohol. The organic oil may comprise glyceryl esters of fatty acids, or triglycerides, such as castor oil, lanolin oil, triisocetyl citrate, $C_{10}$-$C_{18}$ triglycerides, caprylic/capric/triglycerides, coconut oil, mineral oil, almond oil, apricot kernel oil, avocado oil, babassu oil, evening primrose oil, *camelina sativa* seed oil, grape seed oil, macadamia ternifolia seed oil, corn oil, meadowfoam seed oil, mink oil, olive oil, palm kernel oil, safflower oil, sesame oil, soybean oil, sunflower oil, wheat germ oil and *camellia reticulata* seed oil.

Also suitable as the oils are glyceryl esters (excluding fats and oils which are glyceryl esters of fatty acids) which are primarily fatty acid mono-di-and triglycerides which are modified by reaction with other alcohols, for example, acetylated castor oil, glyceryl stearate, glyceryl dioleate, glyceryl distearate, glyceryl trioctanoate, glyceryl distearate, glyceryl linoleate, glyceryl myristate, glyceryl isostearate, PEG castor oils, PEG glyceryl oleates, PEG glyceryl stearates and PEG glyceryl tallowates.

Also suitable as the organic oil are non-volatile hydrocarbons such as isoparaffins, hydrogenated polyisobutene, mineral oil and squalene. Also suitable as the oil are various lanolin derivatives such as acetylated lanolin, acetylated lanolin alcohol, and various fluorinated oils, such as fluoro guerbet esters or perfluropolyethers. Other suitable oils include sorbitan derivatives such as PEG sorbitan beeswax, PEG sorbitan isostearate, PEG sorbitan lanolate, PEG sorbitan laurate, PEG sorbitan oleate, PEG sorbitan palmitate, PEG sorbitan stearate, polysorbates, sorbitan trioleates, sorbitan sesquioleates, sorbitan stearates, sorbitan tristearates, and so on.

Suitable moisturizers (and humectants) in the compositions include glycerin, propylene glycol, butylene glycol, ethylene glycol, polyethylene glycols, having from 4 to 250 repeating ethylene glycol units, and ethoxy-diglycol.

Non-ionic surfactants in the compositions can be alkoxylated derivatives of the following: fatty alcohols, alkyl phenols, fatty acids, fatty acid esters and fatty acid amides, in the $C_{16}$ to $C_{40}$ range, and having from about 1 to about 110 alkoxy groups. The alkoxy groups are selected from the group consisting of $C_2$-$C_6$ oxides and their mixtures, with ethylene oxide, propylene oxide, and their mixtures being the typical alkoxides. The alkyl chain may be linear, branched, saturated, or unsaturated. Of these alkoxylated non-ionic surfactants, the ethoxylated alcohols and propoxylated alcohols are typical. The alkoxylated alcohols may be used alone or in mixtures.

Commercially available, nonionic surfactants are Brij, nonionic surfactants from Uniqema, Willmington. Typically, Brij is the condensation product of aliphatic alcohols with from about 1 to about 54 moles of ethylene oxide, the alkyl chain of the alcohol being typically a linear chain and having from about 8 to about 22 carbon atoms, for example, Brij 72 (i.e., Steareth-2) and Brij 76 (i.e., Steareth-10).

Also useful herein as nonionic surfactants are alkyl glycosides, which are the condensation products of long chain alcohols, e.g. C8-C30 alcohols, with sugar or starch polymers. Commercially available examples of these surfactants include decyl polyglucoside (available as APG<(R)>325 CS) and lauryl polyglucoside (available as APG<(R) >600CS and 625 CS), available from Cognis, Ambler. Other non-ionic surfactants suitable for use in the present invention are glyceryl esters and polyglyceryl esters, including glyceryl monesters, typically glycerly monesters of C16-C22 saturated, unsaturated and branched chain fatty acids such as glyceryl oleate, glyceryl monostearate, glyceryl monoisostearate, glyceryl monopalmitate, glyceryl monobehenate, and mixtures thereof. Also useful herein as nonionic surfactants are sorbitan esters.

Because of the manner in which they are typically manufactured, these sorbitan esters comprise mixtures of mono-, di-, tri-, etc. esters. Representative examples of suitable sorbitan esters include sorbitan monooleate, sorbitan stearates, sorbitan monoisostearate and sorbitan sesquioleate.

For the preparation of the conditioner composition, several cationic components can be used, including cationic quaternary ammonium compounds, amide or amine conditioning agents, and cationic polymers.

Suitable classical cationic conditioning agents include cationic quaternary ammonium salts. Examples of such salts include those having the formula (II):

wherein
R1 is an aliphatic group of 1 to 22 carbon atoms, or aryl (such as phenyl), or alkyl-aryl group having 12 to 22 carbon atoms;
R2 and R3 are each independently an aliphatic group having 1 to 22 carbon atoms; and
R4 is an alkyl group of from 1 to 3 carbon atoms, and X is an anion selected from halogen, acetate, phosphate, nitrate and methyl sulfate radicals.

The aliphatic groups may contain, in addition to carbon atoms, ether linkages as well as amide groups. Suitable quaternary ammonium compounds may be mono-long chain alkyl, di-long chain alkyl, tri-long chain alkyl, and the like. Examples of such quaternary ammonium salts of formula (II) include benzalkonium chloride, benzyl triethyl ammonium chloride, cetyl-triammonium chloride (CTAC), and cetylpyridinium chloride.

Cationic amides are also suitable as further conditioning agents. Also suitable are amidoamine salts, which are the condensation products of fatty acids with polyfunctional amines, for example, those having the formula R'CONH(CH$_2$)$_n$NR1R2 where R'CO is a fatty acyl group such as stearoyl, R1 and R2 are methyl or ethyl, and n is 2 or 3.

Examples of such compounds include stearamido-propyl dimethylamine, see Alzo, Inc. product NECON®. Also suitable are salts of fatty primary, secondary, or tertiary amines, wherein the substituted groups have 12 to 22 carbon atoms. Examples of such amines include dimethyl stearamine, dimethyl soyamine, stearylamine, myristylamine, tridecylamine and -ethyl stearamine.

As cationic components, a variety of cationic polymers are suitable, including quaternized cellulose ethers, copolymers of vinylpyrrolidone, acrylic polymers, including homopolymers or copolymers of dimethyldiallylammonium chloride and acrylamide. Such compounds are sold under MERQUAT® (Merck). Also suitable are various types of homo-or copolymers derived from acrylic or methacrylic acid, acrylamide, methylacrylamide, diacetone-acrylamide.

For the method of treating hair according to the invention, a shampoo composition can be used, but the conditioner composition can also be used without using a shampoo composition. The shampoo compositions are generally comprised of from 1 to 99%, preferably from 5 to 95%, more preferably from 10 to 90% by weight of the total composition of water, and from 0.1 to 99%, preferably from 1 to 95%, more preferably from 5 to 90% by weight of the total composition of a cleansing surfactant. Suitable cleansing surfactants are generally anionic, amphoteric, betaine, or zwitterionic surfactants. Preferably, anionic surfactants include alkyl ether or alkyl ether sulfates such as sodium laureth-sulfate, sodium lauryl sulfate, and other components described above.

The conditioner compositions of the invention generally comprise from 0.1 to 99%, preferably from 0.5 to 95%, more preferably from 1 to 90% by weight, of the total conditioner composition, of water and from 0.1 to 99%, preferably from 0.5 to 95%, more preferably from 1 to 90% by weight of the total conditioner composition of one or more further components. These further components comprise at least one ester of an oxalkylated alkylalkylene diamine of formula (I), and/or a quaternized salt thereof.

The conditioner composition of the invention generally comprises from 0.1 to 10%, preferably from 0.2 to 9%, more preferably from 0.5 to 8% by weight of the total conditioner composition, of at least one ester of an oxalkylated alkylalkylene diamine of formula (I) and/or a quaternized salt thereof.

In one embodiment, the hair conditioner composition comprises 0.5 to 10% by weight, often 0.7 to 8% by weight, of at least one fatty alcohol component, having 6 to 18 carbon atoms. Often, a mixture of at least two fatty alcohol components is used with a total amount of 0.5 to 10% by weight, often 0.7 to 8% by weight.

In one embodiment, the hair conditioner composition comprises 0.5 to 8% by weight of at least one ester of an oxalkylated alkylalkylene diamine of formula (I) and/or a quaternized salt thereof and 0.7 to 8% by weight of a mixture of at least two fatty alcohol components, each having 6 to 18 carbon atoms. Often, this composition further comprises 0.2 to 5% by weight of cetyl trimethylammonium chloride (CTAC)

The conditioner composition of the invention, in addition to water and the oxalkylated alkylalkylene diamine of formula (I) and/or the quaternized salt thereof, often comprises one or more of the following further components:

acidity regulators, antistatic agents, glossers, lubricants, moisturizers, oils, preservatives, sequestrants, strengtheners, sun protectors, further surfactants (such as cetyl trimethylammonium chloride, CTAC) and thermal protectors.

Typical glossers are silicones. Suitable as silicones are volatile or nonvolatile nonionic silicone fluids, silicone resins, and silicone semisolids or solids. Volatile silicones are linear or cyclic silicones having a measureable vapor pressure, which is defined as a vapor pressure of at least 2 mm of mercury at 20° C. Also suitable are water insoluble nonvolatile silicone fluids including polyalkyl siloxanes, polyaryl siloxanes, polyalkylaryl siloxanes, polyether siloxane copolymers, amine-functional silicones, and mixtures thereof.

Typical oils are organic oils, which often are esters of the formula R'CO—OR" presented above. The organic oil component may also comprise glyceryl esters of fatty acids, or triglycerides, coconut oil, almond oil, apricot kernel oil, avocado oil, babassu oil, evening primrose oil, *camelina sativa* seed oil, grape seed oil, macadamia ternifolia seed oil, corn oil, meadowfoam seed oil, mink oil, olive oil, palm kernel oil, safflower oil, sesame oil, soybean oil, sunflower oil, wheat germ oil, and *camellia reticulata* seed oil. Also suitable as the oil component are sorbitan esters and glyceryl esters as described above.

The conditioning composition may also contain further surfactants (not according to formula I), such as those mentioned above. The conditioning composition of the invention often contains at least 0.1% by weight, preferably from 0.1 to 10% by weight, preferably from 0.2 to 5% by weight (of the total composition), of at least one further surfactant, in particular of CTAC.

The conditioning composition of the invention often contains at least about 0.5% by weight, preferably from 0.5 to 10% by weight, often from 0.7 to 8% by weight (of the total composition), of at least one lubricant, in particular a fatty alcohol component, preferably having 6 to 18 carbon atoms. Often, a mixture of at least two fatty alcohol components (e.g. cetyl alcohol and stearyl alcohol with 50:50% by weight) is used with a total amount of 0.5 to 10% by weight, often 0.7 to 8% by weight.

The conditioning composition of the invention often contains at least 0.05% by weight, often from 0.05 to 5% by weight (of the total composition), of at least one oil component. In one embodiment, the conditioning composition contains at least 0.5% by weight, often from 0.5 to 5% by weight (of the total composition) of at least one oil component.

The conditioning composition of the invention can contain from 0.1 to 10% by weight, often from 0.1 to 5%, in particular from 0.5 to 5% by weight (of the total composition), of at least one polymer component (having a molecular weight from 50.000 to 5.000.000 g/mol) from the group of:

polyamines, polyaminoamides or poly (quaternary ammonium) polymers, (such as vinylpyrrolidone/dialkylaminoalkyl acrylate or methacrylate copolymers), or carbomer products (such as Carbopol 980), cellulose ether derivatives containing quaternary ammonium groups, cationic cellulose derivatives such as cellulose copolymers or cellulose derivatives grafted with a water-soluble quaternary ammonium monomer quaternized polysaccharides homopolymer of dimethyldiallylammonium chloride, (such as MERCK products MERQUAT® 100 or MERQUAT® 550)

quaternary polymers of vinylpyrrolidone and of vinylimidazole, cationic polysiloxanes such as described in U.S. Pat. No. 4,185,087 poly (quaternary ammonium) polymers.

The conditioning composition of the invention can contain from 0.1 to 10% by weight, often from 0.2 to 5% by weight, in particular 0.5 to 5% by weight (of the total composition), of at least one rheology modifying agent, in particular gelling and thickening agent. Examples are cellulosic thickeners, for example, hydroxyethyl-cellulose, hydroxypropylcellulose, and carboxymethylcellulose, guar gum, such as hydroxypropylguar, gums of microbial origin, such as xanthan gum and scleroglucan gum, and synthetic thickeners, such as crosslinked homo- or copolymers of acrylic acid and/or of acrylamidopropanesulphonic acid. Other rheology modifying agents include fatty acid amides such as coconut diethanolamide and monoethanolamide, and oxyethylenated monoethanolamide of carboxylic acid alkyl ether.

In the method of the invention the conditioner composition is applied to the (wet) hair. Before the conditioner composition is applied, according to one embodiment, a shampoo composition can be applied to the hair for a period of time ranging from about 30 seconds to 5 minutes. The shampoo composition is then rinsed from the hair using water.

The conditioner composition comprising the esters of an oxalkylated alkylalkylene diamines of formula (I) and/or a quaternized salts thereof (and often the lubricant), is combined with water and the mixture is then applied to the hair. The mixture may be left on the hair for about 1 to 10 minutes, or rinsed immediately, or as recommended in the instructions given in the kit. After the indicated amount of time has elapsed, the mixture is rinsed off the hair with water.

Finally, a post-treatment composition can be applied to the hair and may or may not be rinsed off. Following the application of the post-treatment composition, the hair can be brought to the style as desired.

The shampoo composition and/or the conditioner composition, and/or the post-treatment composition can be provided in a kit such that they may be used on a daily, bi-weekly or weekly basis, depending on the needs of the consumer. Preferably, the shampoo and conditioner compositions are used on a weekly to bi-weekly basis.

The invention is further illustrated by the following examples and the claims.

EXAMPLE 1

Preparation of a Salt with Two Quaternized N-atoms

The following compound 13-SK009 was prepared as following:

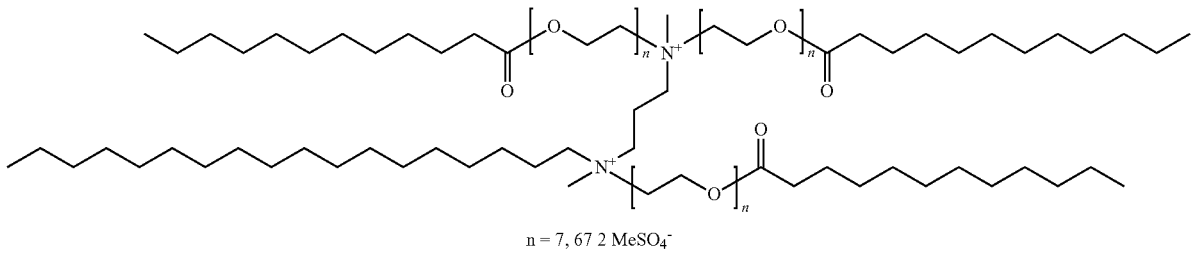

n = 7, 67 2 MeSO$_4^-$ 509.2 g (0.250 mol) of a compound with the formula (I) with R=C-Chain derived from tallow fatty acid (C16/C18), a=0, m=3, A=—C$_2$H$_4$—, u+v+w=23, Z$^2$=Z$^3$=Z$^4$=C-Chain derived from cocos fatty acid (C12/C14) were initially charged in a 1 L-flask equipped with a reflux condenser and a thermometer and heated to 60° C.

While stirring, 62.4 g (0.495 mol) dimethyl sulfate were added dropwise within 30 minutes. During that period, the temperature raised to 80° C. The reaction mixture was stirred for 5 h at 80° C. After cooling to room temperature, 530 g product (salt with two quaternized N-atoms) were obtained (Bas.N<0.1%) as clear yellow-brown liquid. The group "Me" in the above formula denotes a methyl group.

EXAMPLE 2

Preparation of a Salt with (on Average) One Quarternized N-atom

The following compound 13-CK068 (mixture) was prepared as following:

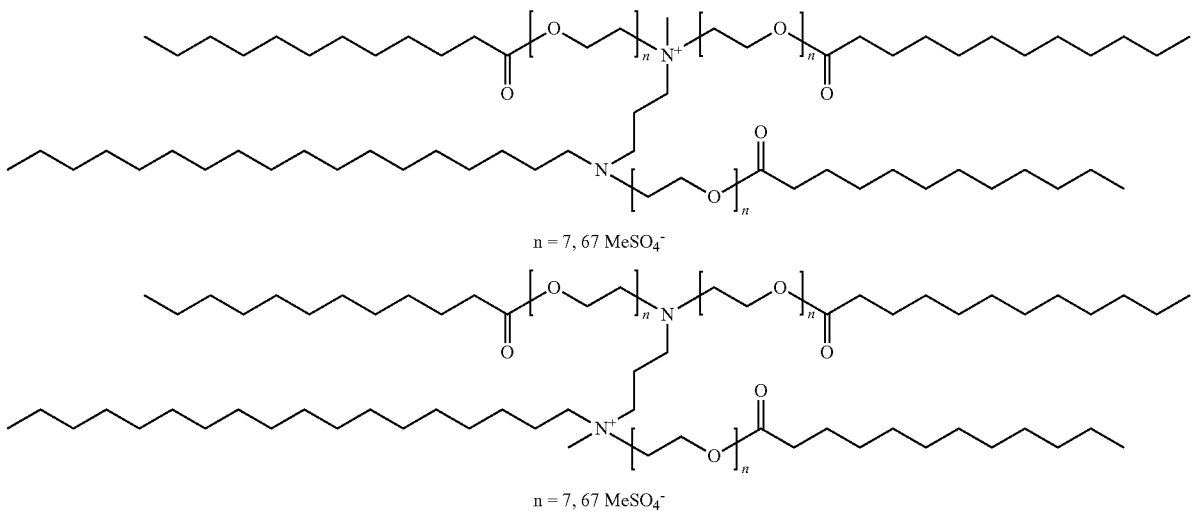

n = 7, 67 MeSO$_4^-$ n = 7, 67 MeSO$_4^-$ 203.7 g (0.1 mol) of a compound with the formula (I) with R=C-Chain derived from tallow fatty acid (C16/C18), a=0, m=3, A=—$C_2H_4$—, u+v+w=23, $Z^2=Z^3=Z^4$=C-Chain derived from cocos fatty acid (C12/C14) were initially charged in a 1 L-flask equipped with a reflux condenser and a thermometer and heated to 60° C.

While stirring, 12.3 g (0.1 mol) dimethyl sulfate were added drop wise within 30 minutes. During that period, the temperature raised to 80° C. The reaction mixture was stirred for 5 h at 80° C. After cooling to room temperature, 207.6 g product were obtained (Bas.N=0.67%) as clear yellow-brown liquid.

EXAMPLE 3

Preparation of a Salt with Two Quaternized N Atoms

The following compound (14-CK050) was prepared corresponding to the method of Example 1:

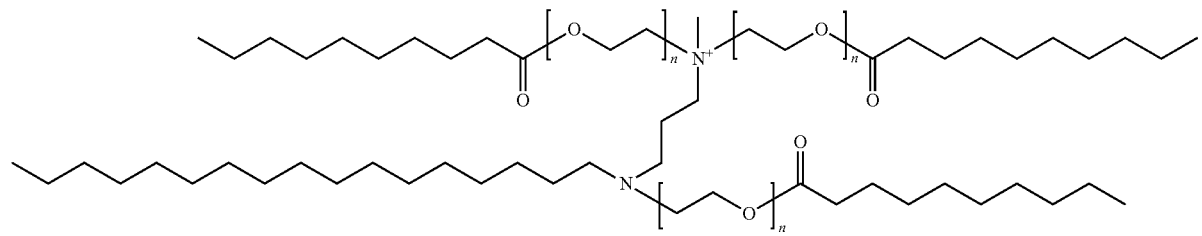

n=2.5; $2CH_3SO_4^{31}$; R=C-chain derived from tallow fatty acid ($C_{16}/C_{18}$), a=0, m=3, A=—$C_2H_4$—, u+v+w=7.5, $Z^2=Z^3=Z^4$=C-chain derived from caprylic acid ($C_8$)

EXAMPLE 4

Preparation of a Salt with Two Quaternized N Atoms

The following compound (14-CK097) was prepared corresponding to the method of Example 1:

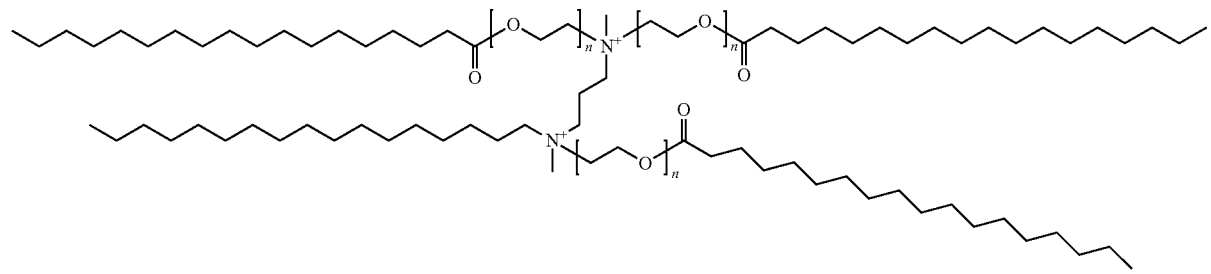

n=5.00; $2CH_3SO_4^-$; R=C-chain derived from tallow fatty acid ($C_{16}/C_{18}$), a=0, m=3, A=—$C_2H_4$—, u+v+w=15, $Z^2=Z^3=Z^4$=C-chain derived from stearic acid ($C_{18}$)

EXAMPLES 5 to 9

Preparation of Conditioner Compositions

The hair conditioner compositions (E5 to E9) were prepared by mixing the following components (Table 1).

TABLE 1

Composition of hair conditioners containing molecules of Examples 1 to 4.

| Formulation/ Example | New component | New component (%) | CTAC (%) | Cetearyl alcohol (%) | Silicone DC PMX 200 (%) |
| --- | --- | --- | --- | --- | --- |
| Example 5 | 13-SK009 (Example 1) | 2.0 | 0 | 4.00 | 0.2 |
| Example 6 | 13-CK068 (Example 2) | 2.0 | 0 | 4.00 | 0.2 |
| Example 7 | 14-CK050 (Example 3) | 1.8 | 0.2 | 4.0 | 0.2 |
| Example 8 | 14-CK097 (Example 4) | 1.8 | 0.2 | 4.0 | 0.2 |
| Example 9 | 14-CK097 (Example 4) | 2.0 | 0 | 4.0 | 0.2 |

All % are based on the weight of the composition.

For all samples, pH of the water based compositions was adjusted between 3.5 and 5.

EXAMPLE 10

Use of the Conditioner Composition

The studies were conducted with hair swatches (using dark brown, straight European hair tresses, 12 cm long, and 4 h bleached European hair, 12 cm long, both from Kerling, Germany).

These hair swatches were pre-treated (base wash with a 14% by weight sodium lauryl ether sulfate (SLES) solution) and then treated with a classical, silicone-free shampoo composition, and then with one of the conditioner compositions E5 to E9, according to the steps:
a) applying the shampoo composition onto the hair;
b) washing the hair with the shampoo composition;
c) removing the shampoo composition from the hair;
d) applying the conditioner composition of Examples 5 to 9 onto the hair;

e) removing said conditioner composition from the hair.

During rinsing the conditioner, for all examples E5 to E9, hair became detangled, had a smooth feel under running water and a pleasant tactile profile. Wet hair was tested for combing force (using an MTT175 tensile tester from Diastron, UK). Afterwards, the swatches were left to dry hanging in air at room temperature. The dry hair after all treatments with conditioner compositions E5 to E9 also showed good tactile results and led to nice hair appearance.

After the use of the hair conditioning system, comprising a pre-treatment with shampoo and a conditioner treatment, the hair probes were tested for hair shine (using a Samba Hair System, from Bossa Nova Tech) and dry combing force (using an MTT175 tensile tester from Diastron, UK).

Regarding hair shine, this measurement technique allows for quantitative evaluation of the light intensity reflected from hair swatches mounted on a drum in a half-circle arrangement. The technique selectively analyzes the following components:
  First reflection (SHINE): from the surface of the fibers, creates a shine band on hair
  Second reflection (CHROMA): reflection of the transmitted light off the bottom surface of the fibers—creates a band carrying color information specific to the fiber
  DIFFUSED LIGHT results from the internal scattering, and corresponds to 'bulk hair' shine and color intensity.

Conventionally, maximum values of each peak are compared for samples treated with different materials.

Combing results and hair shine data for hair treated with the conditioners of Examples 5 to 9 are summarized in Table 2. As references, conditioners containing CTAC at 2% (active level) or BTAC at 2% (active level) were used, with the same levels of cetearyl alcohol (4% active) and 0.2% silicone oil (Dow Corning PMX 200).

TABLE 2

Performance results of hair conditioners of Examples 5 to 9.

| Conditioner | wet combing force, virgin hair (average), gmf | wet combing force, bleached hair (average), gmf | dry combing force, virgin hair (max), gmf | dry combing force, bleached hair (max), gmf | hair shine, virgin hair, BossaNovaluster values |
|---|---|---|---|---|---|
| CTAC 2% | — | 12.1 | 140.8 | 117.2 | 15.5 |
| BTAC 2% | 10.7 | — | — | — | — |
| Example 5 | — | — | 92.9 | 28.7 | 16.0 |
| Example 6 | — | — | 65.2 | 28.8 | 16.6 |
| Example 7 | 8.8 | 11.9 | — | 58.7 | 16.3 |
| Example 8 | 9.7 | — | — | 43.0 | 17.5 |
| Example 9 | 10.2 | — | — | 66.9 | 16.1 |

It is seen from the data of Table 2 that the use of the new compositions described here significantly improves the properties of hair conditioner products. In particular, the lowering of wet and dry combing force has been observed for both virgin and bleached (damaged) hair, in comparison to typical market benchmarks. For consumers, this corresponds to easier combing, less tangling and better alignment of hair, which further leads to easier styling. Additionally, hair shine has been improved by applying a composition comprising an oxalkylated alkylalkylene diamine of formula (I).

The invention claimed is:

1. A hair conditioning composition comprising 0.1 to 10% by weight of an oxalkylated alkylalkylene diamine of formula (I)

$$R-N\begin{array}{l}(CH_2)_m-N\begin{array}{l}(A-O)_u-Z^4\\(A-O)_v-Z^3\end{array}\\(CH_2)_m-N\underset{a}{\overline{\phantom{|}}}(A-O)_w-Z^2\\\phantom{(CH_2)_m-N}(A-O)_x-Z^1\end{array} \quad (I)$$

wherein
R is $C_8$-$C_{24}$-alkyl or $C_8$-$C_{24}$-alkenyl
A is —$C_2H_4$— or —$C_3H_6$—,
$Z^1$ is —C(O)—R', wherein R' is $C_5$-$C_{35}$-alkyl or $C_5$-$C_{35}$-alkenyl,
$Z^2$ is —C(O)—R", wherein R" is $C_5$-$C_{35}$-alkyl or $C_5$-$C_{35}$-alkenyl,
$Z^3$ is —C(O)—R'", wherein R'" is $C_5$-$C_{35}$-alkyl or $C_5$-$C_{35}$-alkenyl,
$Z^4$ is —C(O)—R"", wherein R"" is $C_5$-$C_{35}$-alkyl or $C_5$-$C_{35}$-alkenyl,
a is 0 or 1,
m is 2 or 3,
u, v, x and w are each independently numbers from 1 to 9,
where if a=0 the sum of u, v, and w is from 3 to 30, and
where if a=1 the sum of u, v, w and x is from 4 to 35,
or a quaternized salt thereof, and
0.5 10% by weight of a fatty alcohol component, having 6 to 18 carbon atoms.

2. The hair conditioning composition according to claim 1, comprising an oxalkylated alkylalkylene diamine of formula (I), wherein
R is $C_8$-$C_{24}$-alkyl or $C_8$-$C_{24}$-alkenyl
A is a group —$C_2H_4$—
$Z^1$ is —C(O)—R', wherein R' is $C_8$-$C_{18}$-alkyl or $C_8$-$C_{18}$-alkenyl
$Z^2$ is —C(O)—R", wherein R" is $C_8$-$C_{18}$-alkyl or $C_8$-$C_{18}$-alkenyl $Z^3$ is —C(O)—R''', wherein R''' is $C_8$-$C_{18}$-alkyl or $C_8$-$C_{18}$-alkenyl $Z^4$ is —C(O)—R'''', wherein R'''' is $C_8$-$C_{18}$-alkyl or $C_8$-$C_{18}$-alkenyl a is 0 m is 3, u, v and w are each independently numbers from 3 to 9, where the sum of u, v and w is from 6 to 30, or a quaternized salt thereof, where the salt is formed by quaternizing one or two of the nitrogen atoms of the compound of formula (I).

3. The hair conditioning composition according to claim 1, comprising an oxalkylated alkylalkylene diamine of formula (I), wherein R is $C_8$-$C_{18}$-alkyl or $C_8$-$C_{18}$-alkenyl A is a group —$C_2H_4$—

$Z^1$, $Z^2$, $Z^3$ and $Z^4$ are the same and are —C(O)—R' with

R' being $C_8$-$C_{18}$-alkyl or $C_8$-$C_{18}$-alkenyl a is 0, m is 3 u, v, and w are each independently numbers from 3 to 9, where the sum of u, v and w is from 6 to 30, or a quaternized salt thereof, where the salt is formed by quaternizing one or two of the nitrogen atoms of the compound of formula (I).

4. The hair conditioning composition according claim 1, comprising a salt of an ester of an oxalkylated alkylalkylene diamine of formula (I).

5. A method of preparing a hair conditioning composition, comprising the step of mixing an oxalkylated alkylalkylene diamine of formula (I),

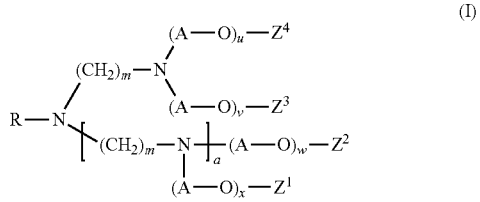

(I)

wherein

R is $C_8$-$C_{24}$-alkyl or $C_8$-$C_{24}$-alkenyl

A is —$C_2H_4$— or —$C_3H_6$—, $Z^1$ is —C(O)—R', wherein R' is $C_5$-$C_{35}$-alkyl or $C_5$-$C_{35}$-alkenyl, $Z^2$ is —C(O)—R'', wherein R'' is $C_5$-$C_{35}$-alkyl or $C_5$-$C_{35}$-alkenyl, $Z^3$ is —C(O)—R''', wherein R''' is $C_5$-$C_{35}$-alkyl or $C_5$-$C_{35}$-alkenyl, $Z^4$ is —C(O)—R'''', wherein R'''' is $C_5$-$C_{35}$-alkyl or $C_5$-$C_{35}$-alkenyl, a is 0 or 1, m is 2 or 3, u, v, w and x are each independently numbers from 1 to 9, where if a=0, the sum of u, v and w is from 3 to 30, and where if a=1, the sum of u, v, w and x is from 4 to 35, or a quaternized salt thereof, and a fatty alcohol component, having 6 to 18 carbon atoms.

6. A method of conditioning the hair, comprising the steps of applying a hair conditioner composition onto wet hair and removing the conditioner composition from the hair, wherein the hair conditioner composition comprises
an ester of an oxalkylated alkylalkylene diamine of formula (I),

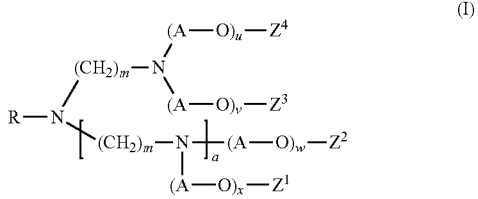

(I)

wherein

R is $C_8$-$C_{24}$-alkyl or $C_8$-$C_{24}$-alkenyl

A is —$C_2H_4$— or —$C_3H_6$—, $Z^1$ is —C(O)—R', wherein R' is $C_5$-$C_{35}$-alkyl or $C_5$-$C_{35}$-alkenyl, $Z^2$ is —C(O)—R'', wherein R'' is $C_5$-$C_{35}$-alkyl or $C_5$-$C_{35}$-alkenyl, $Z^3$ is —C(O)—R''', wherein R''' is $C_5$-$C_{35}$-alkyl or $C_5$-$C_{35}$-alkenyl, $Z^4$ is —C(O)—R'''', wherein R'''' is $C_5$-$C_{35}$-alkyl or $C_5$-$C_{35}$-alkenyl, a is 0 or 1, m is 2 or 3, u, v, w and x are each independently numbers from 1 to 9, where if a=0, the sum of u, v and w is from 3 to 30, and where if a=1, the sum of u, v, w and x is from 4 to 35, or a quaternized salt thereof, and a fatty alcohol component, having 6 to 18 carbon atoms.

7. The method of conditioning the hair according to claim 6, further comprising the following steps:

a) applying a shampoo composition onto the hair;

b) washing the hair with the shampoo composition;

c) removing the shampoo composition from the hair;

prior to applying a hair conditioner composition onto wet hair and removing the conditioner composition from the hair.

8. The method of claim 6, wherein the hair conditioner composition comprises a quaternized salt of an oxalkylated alkylalkylene diamine of formula (I), where the salt is quaternized at one or two of the nitrogen atoms of the compound of formula (I).

9. The method of claim 6, wherein the hair conditioner composition further comprises as a lubricant a fatty alcohol component, having 6 to 18 carbon atoms.

10. The method of claim 6, wherein the hair conditioner composition further comprises a silicone, and a further surfactant.

11. The method of claim 6, wherein the hair conditioner composition further comprises a further surfactant which is selected from the group consisting of non-polymeric, cationic quaternary ammonium compounds.

12. The method of claim 6, wherein the hair conditioner composition is applied to the hair on a weekly to bi-weekly basis following initial treatment of the hair with a shampoo composition.

13. The hair conditioner composition according to claim 1, wherein at least one of $Z^1$, $Z^2$, $Z^3$, and $Z^4$ is $C_8$-$C_{18}$-alkyl or $C_8$-$C_{18}$-alkenyl.

14. The hair conditioner composition according to claim 1, wherein the quaternized salt is formed by using an alkylating agent selected from the group consisting of dimethyl sulfate, diethyl sulfate, dimethyl carbonate, diethyl carbonate, methyl chloride, ethyl chloride, methyl bromide, ethyl bromide, methyl iodide, and ethyl iodide.

15. The method of claim 6, wherein the hair conditioner composition further comprises cetyl trimethylammonium chloride.

16. The hair conditioning composition according to claim 1, comprising an oxalkylated alkylalkylene diamine of formula (I), wherein the oxalkylated alkylalkylene diamine of formula (I) is a quaternized salt.

* * * * *